(12) United States Patent
Castaldi et al.

(10) Patent No.: US 6,979,736 B2
(45) Date of Patent: Dec. 27, 2005

(54) PROCESS FOR THE PREPARATION OF BENAZEPRIL HYDROCHLORIDE

(75) Inventors: Graziano Castaldi, Briona (IT); Gabriele Razzetti, Sesto S. Giovanni (IT); Simone Mantegazza, Milan (IT)

(73) Assignee: Dipharma S.p.A., Mereto di Tomba (IT)

( * ) Notice: Subject to any disclaimer, the term of this patent is extended or adjusted under 35 U.S.C. 154(b) by 0 days.

(21) Appl. No.: 10/513,142

(22) PCT Filed: Apr. 25, 2003

(86) PCT No.: PCT/EP03/04343

§ 371 (c)(1),
(2), (4) Date: Nov. 2, 2004

(87) PCT Pub. No.: WO03/092698

PCT Pub. Date: Nov. 13, 2003

(65) Prior Publication Data

US 2005/0203294 A1      Sep. 15, 2005

(30) Foreign Application Priority Data

May 3, 2002    (IT) ................ MI2002A0934

(51) Int. Cl.[7] ............... C07D 223/16; C07D 405/12; C07D 413/04
(52) U.S. Cl. ................................ 540/523
(58) Field of Search ............................. 540/523

(56) References Cited

U.S. PATENT DOCUMENTS 4,410,520 A    10/1983    Watthey

FOREIGN PATENT DOCUMENTS

EP        0 206 993        12/1986

*Primary Examiner*—Bruck Kifle
(74) *Attorney, Agent, or Firm*—Young & Thompson

(57) ABSTRACT

A process for the preparation of benazepril hydrochloride (2) starting from the Michael adduct (14), obtained reacting compounds of formula (11) and (13), as defined in the disclosure

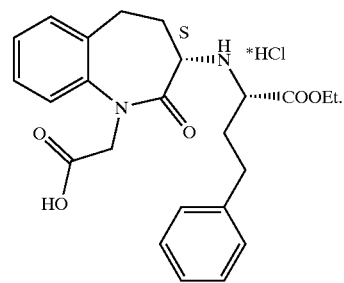

(2)

19 Claims, No Drawings

PROCESS FOR THE PREPARATION OF BENAZEPRIL HYDROCHLORIDE

This application is a 371 of PCT/EP03/04343, filed Apr. 25, 2003.

FIELD OF THE INVENTION

The present invention relates to antihypertensive agents, in particular ACE-inhibitors.

PRIOR ART

Benazepril (1), namely [S—(R*,R*)]3-[[1-(ethoxycarbonyl)-3-phenylpropyl]-amino]-2,3,4,5-tetrahydro-2-oxo-1-H-1-benzazepin-1-acetic]acid, is an antihypertensive compound belonging to the class of ACE-inhibitors, which are compounds inhibiting the angiotensine converting enzyme. Benazepril is usually employed in therapy in the form of hydrochloride (2).

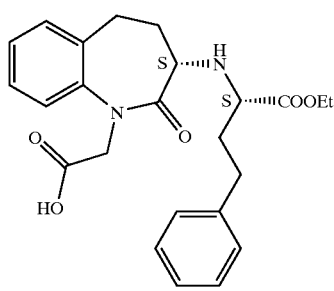

The preparation of benazepril disclosed in U.S. Pat. No. 4,410,520 and J. Med. Chem. 1985, 28, 1511–1516, reported in Scheme 1, involves the reductive amination of ethyl 2-oxo-4-phenyl butyrate (3) with (3S)-3-amino-1-carboxymethyl-2,3,4,5-tetrahydro-1H-benzazepin-2-one (4) promoted by sodium cyanoborohydride. The two resulting benazepril isomers are obtained in a 7:3 diastereomeric ratio. Following treatment with hydrochloric acid gas and recrystallization, the hydrochloride is isolated in a 95:5 diastereomeric ratio and in 25% yield. The main drawback of this method is that it requires the use of sodium cyanoborohydride, which is a toxic reagent, and furthermore it affords the hydrochloride in too low a diastereomeric ratio to be marketed.

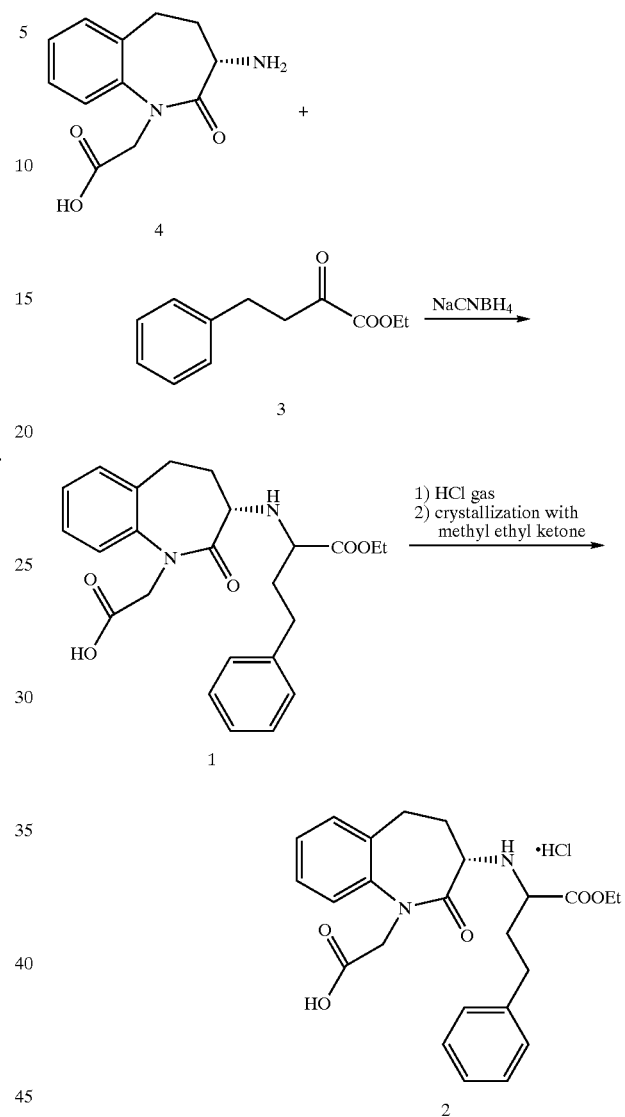

U.S. Pat. No. 4,410,520 discloses other methods for the preparation of benazepril, as reported in Scheme 2, which however make use of precursors difficult to obtain and afford diastereomeric mixtures difficult to separate.

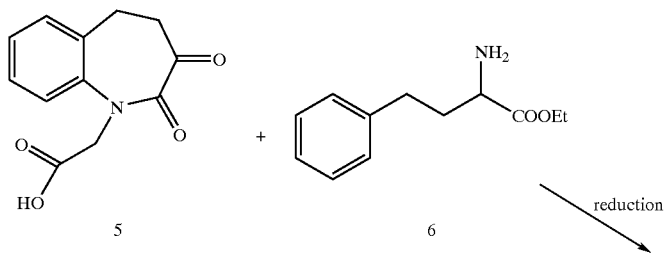

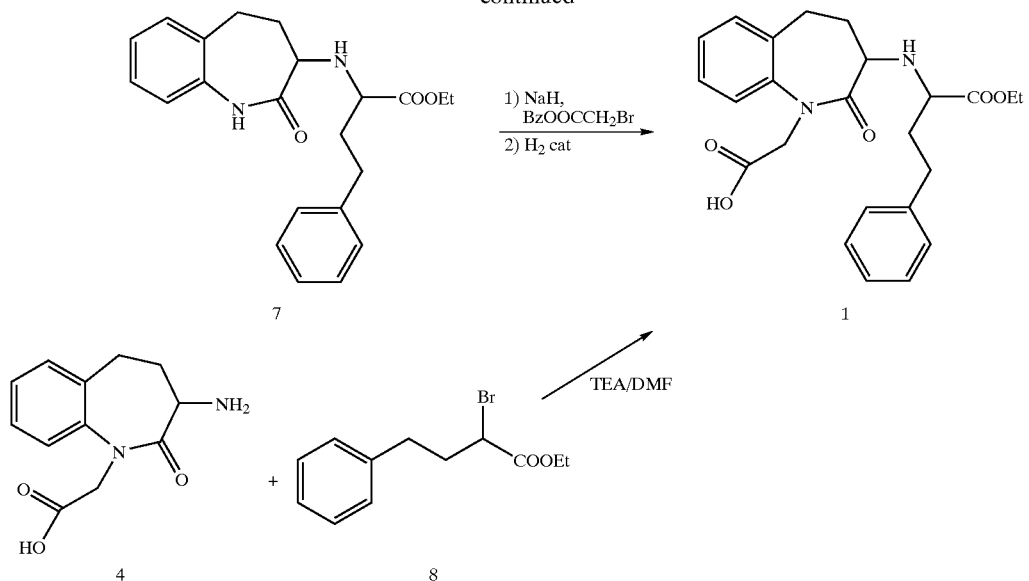

An alternative method to those reported above was disclosed in EP 206993. It involves the nucleophilic substitution of (3S)-3-amino-1-t-butoxycarbonylmethyl-2,3,4,5-tetrahydro-1H-benzazepin-2-one (11), using N-methylmorpholine as solvent/reagent, on the chiral substrate ethyl (2R)-2-(4-nitrobenzenesulfonyl)-4-phenyl butyrate (10) which is in turn prepared starting from ethyl 2-oxo-4-phenyl butyrate (3), by stereoselective hydrogenation in the presence of chiral bases (e.g. cinchonidine) (scheme 3), which step makes the whole process rather complex. The reaction between compounds (10) and (11) is carried out at 80° C. for more than 6 hours. Treatment with hydrochloric acid gas and precipitation with ethyl acetate directly afford Benazepril hydrochloride in a S,S:R,S=99.7:0.3 diastereomeric ratio.

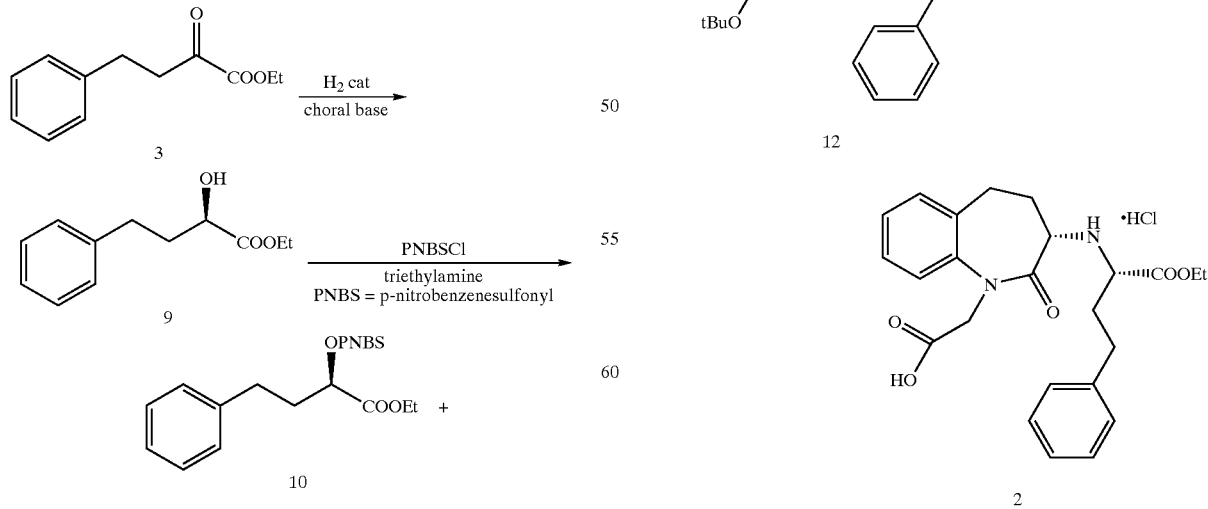

DETAILED DISCLOSURE OF THE INVENTION

The present invention relates to a process for the preparation of benazepril hydrochloride, reported in Scheme 4, which makes use of (3S)-3-amino-1-t-butoxycarbonylmethyl-2,3,4,5-tetrahydro-1H-benzazepin-2-one (11) as a precursor.

The process comprises the following steps:
a) reacting (3S)-3-amino-1-t-butoxycarbonylmethyl-2,3,4,5-tetrahydro-1H-benzazepin-2-one (11) with a 3-benzoyl acrylic acid ester (13) to give the corresponding Michael adduct (14);
b) transforming the adduct (14) to give 3-[[1-(carboxy)-3-phenyl-propyl]-amino]-1-t-butoxycarbonylmethyl-2,3,4,5-tetrahydro-1H-benzazepin-2-one (15);
c) crystallizing the S,S isomer of compound (15);
d) esterifying compound (15) to give 3-[[1-(ethoxycarbonyl)-3-phenyl-propyl] amino]-1-t-butoxycarbonylmethyl-2,3,4,5-tetrahydro-1H-benzazepin-2-one (12);
e) treating compound (12) with hydrochloric acid gas to give benazepril hydrochloride.

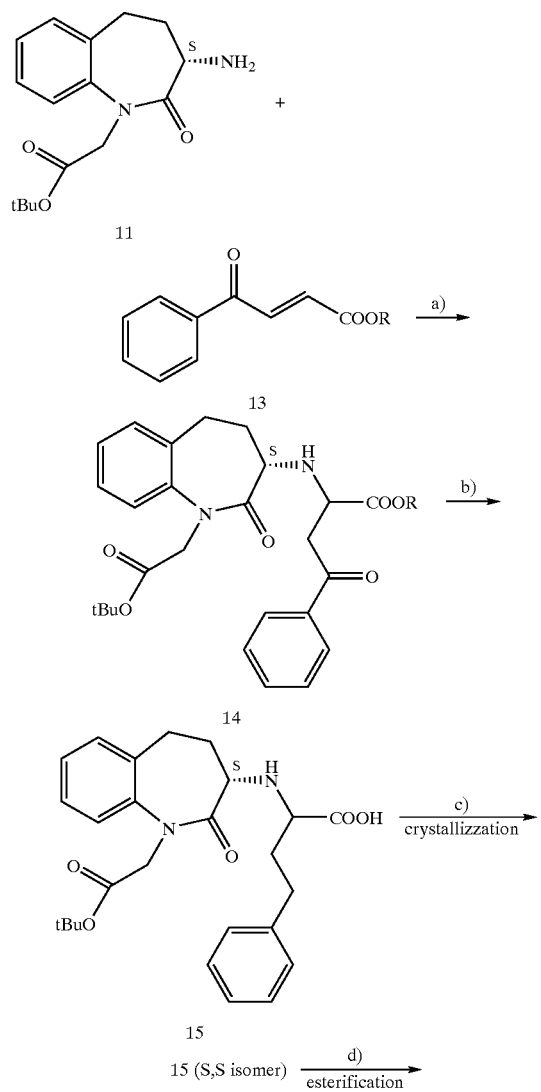

Scheme 4

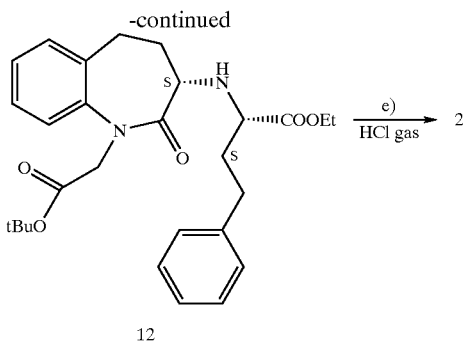

In compounds of formula (13) and (14) R is a straight or branched $C_1$–$C_6$ alkyl group or a benzyl group.

Step a) is carried out reacting compound (11) with compounds (13) in molar amounts ranging from 0.5 to 2, preferably from 0.9 to 1.1, in organic solvents selected for example from aromatic solvents, preferably toluene, chlorinated solvents, preferably dichloromethane, esters, preferably ethyl acetate, ethers, preferably diethyl ether and tetrahydrofuran, dipolar aprotic solvent, preferably dimethylformamide, aliphatic solvents, preferably cyclohexane, alcohols, preferably methanol, ketones, preferably acetone. According to preferred embodiments of the invention, the reaction is carried out in toluene or in ethyl acetate, most preferably in toluene. The reaction is carried out at temperatures ranging from –10° C. to 80° C., preferably from 0° C. to 25° C. Compounds (14) are obtained in high yields and consist of a mixture of two S,S and S,R diastereomers, in a ratio which mainly depends on the solvent used, as reported in Table I for compound (14a), in which R is ethyl (obtained in a yield higher than 95%). The best results are obtained with a polar solvents such as toluene.

TABLE 1

Relationship between solvent - (14a) diastereomer ratio

| Solvent | 14a (R = $C_2H_5$) S,S/S,R isomers ratio |
|---|---|
| Dichloromethane | 65:35 |
| Toluene | 75:25 |
| Dimethylformamide | 60:40 |
| Methanol | 58:42 |
| Ethyl acetate | 60:40 |
| Ethyl acetate under reflux | 40:60 |
| Cyclohexane | 73:27 |
| Water | No reaction |
| Hexane | No reaction |

The Michael adduct (14) is a novel compound and is also part of the present invention.

The transformation of step b) can be carried out as follows:

b1) compound (14) is hydrogenated in the same solvent as used for step a) in the presence of a catalyst selected for example from Pd, Pt, Rh, Ru, Cu, in molar amounts ranging from 0.01 to 1, preferably from 0.01 to 0.1, on supports selected for example from charcoal, alumine, barium sulfate, calcium carbonate, at temperatures ranging from –10° C. to 80° C., preferably from 0° C. to 30° C., at a hydrogen pressure ranging from 1 atm to 40 atm, preferably from 2 atm to 10 atm, to give a compound of formula (16), in which R has the meanings as defined above (scheme 5). According to a preferred embodiment of the invention, the reaction is carried out without isolating compound (14), using ethyl acetate or toluene as solvent, preferably toluene, and Pd on charcoal as catalyst.

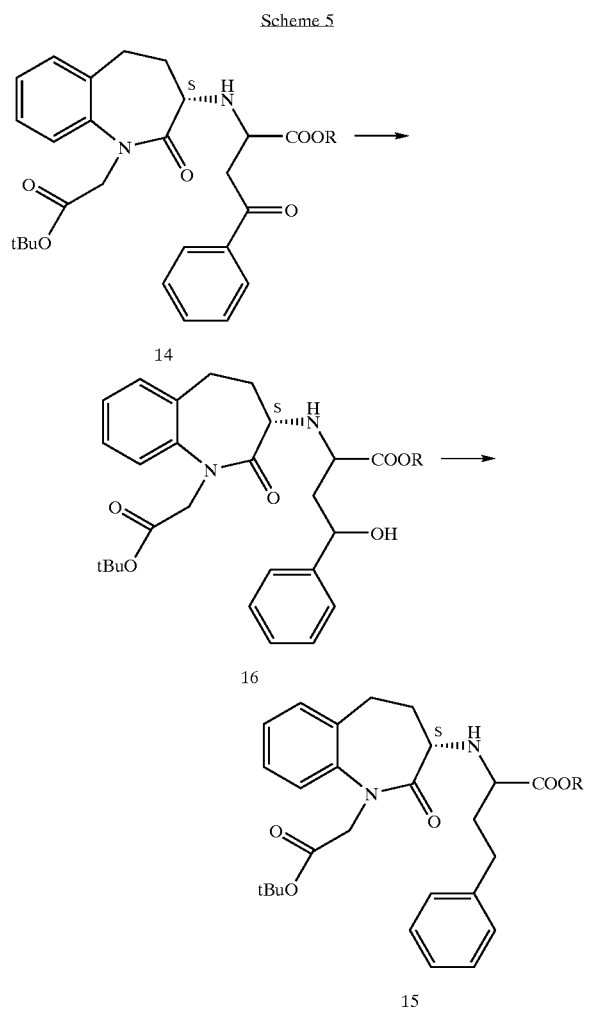

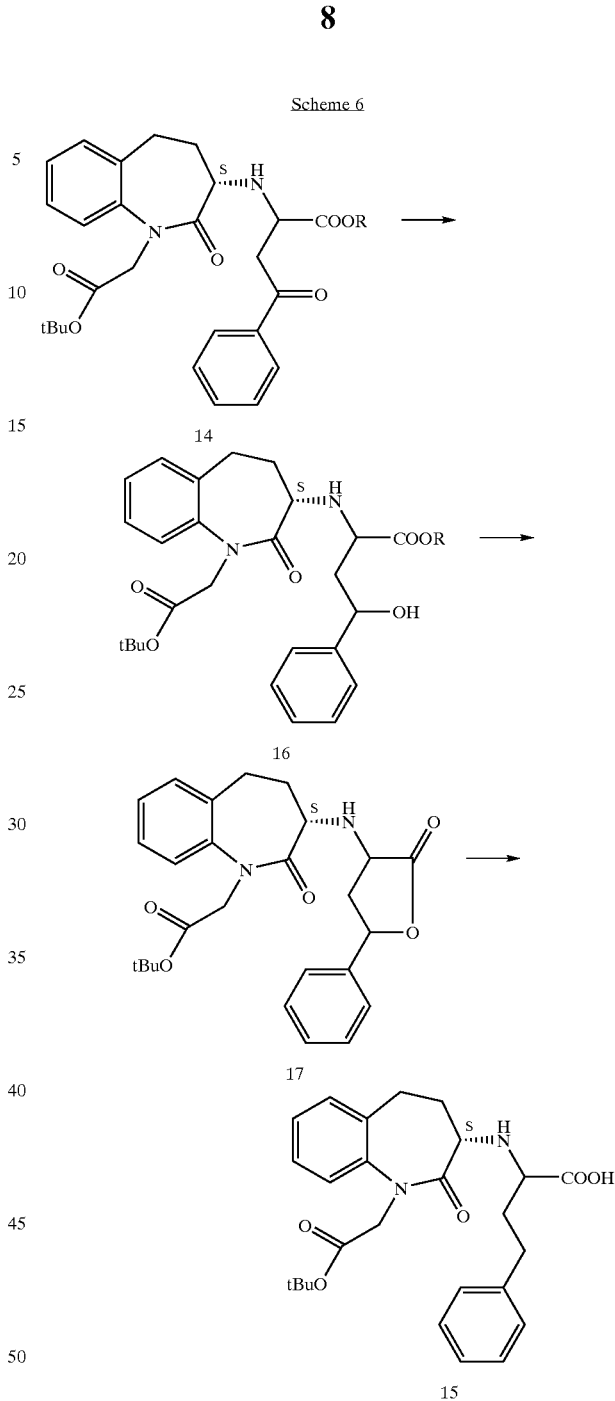

The resulting intermediate (16) consists of a mixture of four diastereomers (SSS, SRS, SSR, SRR); this compound is also novel and it forms part of the invention.

Transformation into (15) is completed preferably without isolating compound (16), but treating the mixture from the above reaction with a mineral or organic acid and carrying out the catalytic reduction as described above. The mineral acid is preferably sulfuric acid, while the organic acid is preferably selected from acetic acid, trifluoroacetic acid, methanesulfonic acid and toluenesulfonic acid, more preferably acetic acid.

b2) Compound (14) is hydrogenated to compound (16) as described in b1. The catalyst is filtered off, then the solution containing (16) is added with acetic acid in molar ratios ranging from 0.1 to 100 with respect to (16) and left to react at temperatures ranging from 0 to 120° C., preferably from 15 to 60° C. The resulting lactone (17) is a novel compound and is also part of the present invention.

Similarly to the parent compound (16), compound (17) consists of a diastereomeric mixture (SSS, SSR, SRR, SRS). Transformation of (17) into (15) can be carried out by catalytic hydrogenation under the same conditions as used to transform (14) into (16) or by "hydrogen transfer" reaction. Particularly useful hydrogen donors are cyclic ethers, cyclohexene, cyclohexadiene, methylcyclohexene, limonene, dipentene, mentene, hydrazine, phosphinic acid and derivatives, indoline, ascorbic acid, formic acid and the sodium or ammonium salts thereof, secondary alcohols such as isopropanol, in molar ratios from 1.5 to 50, preferably from 1.5 to 10. The use of cyclohexene in molar ratios from 1.5 to 3 or ammonium formate in molar ratios from 1 to 4 is preferred, in particular the latter one b3) Compound (14) is treated with sodium borohydride in molar ratios from 0.25 to 5, preferably from 0.5 to 1.5, at temperatures from 0 to 80° C., preferably from 10 to 30° C. If necessary, sodium borohydride may be dissolved by addition of methanol as cosolvent, or the reactive can be dissolved in a 0.1 M NaOH solution, subsequently adding a phase transfer catalyst such as tetrabutylammonium chloride. This reaction directly affords lactone (17), which is transformed into (15) as described in b2 (scheme 7).

from −10° C. to 80° C., preferably from 0° C. to 25° C. According to a preferred embodiment of the invention, the solvent is toluene. The reaction of compound (15) with carbonyldiimidazole affords two reactive species (scheme 8). A small percentage consists of imidazolide (18), which is usually obtained by reaction of carbonyldiimidazole with a carboxylic acid, while the main part consists of the activated heterocyclic compound (19), as evidenced by HPLC and NMR analysis of the mixture.

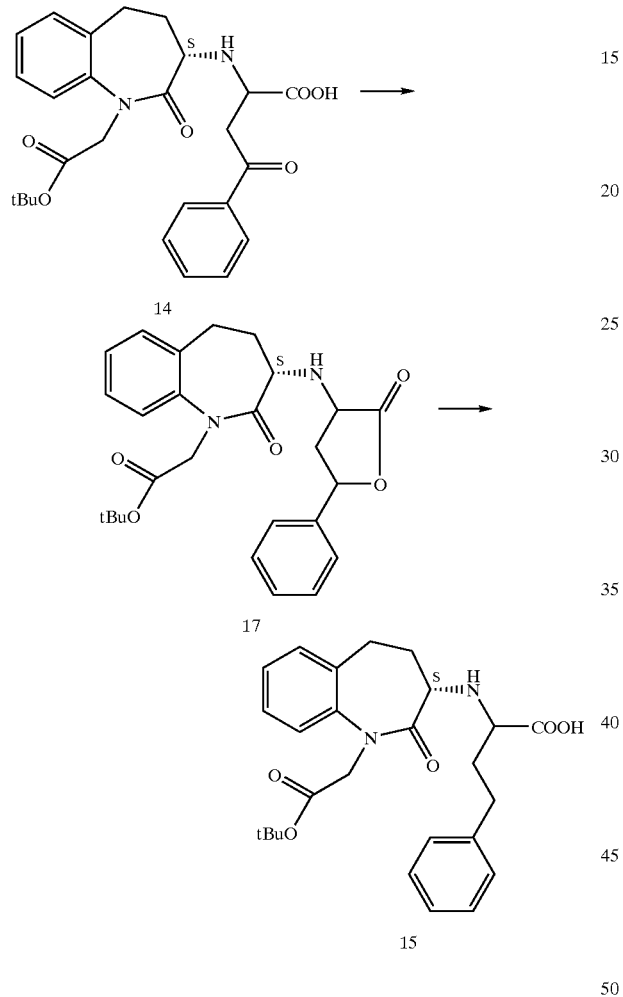

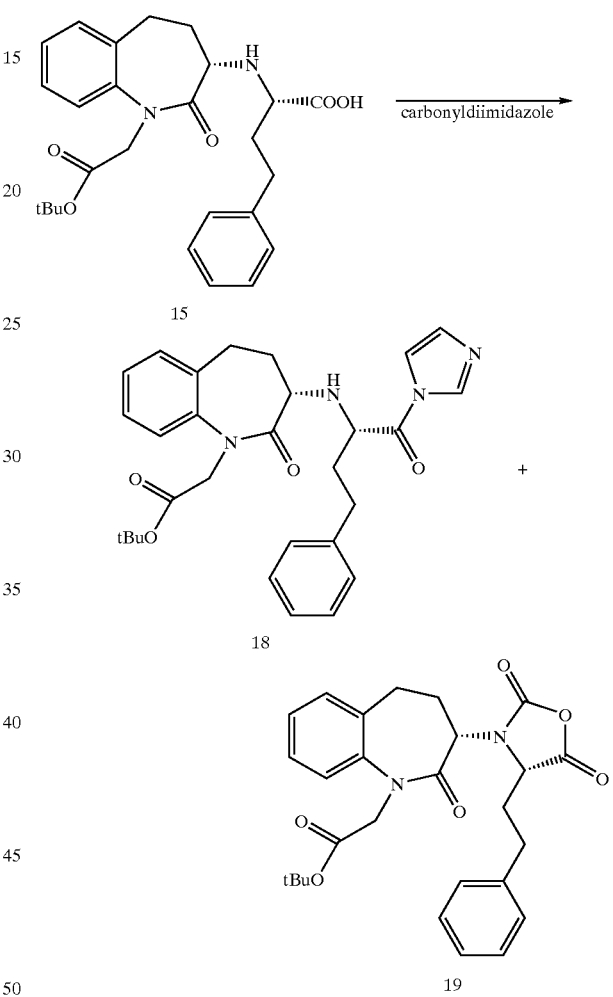

The resulting compound (15), consisting of a S,S and S,R diastereomeric mixture, is crystallized (step c) by treatment with an organic solvent selected from an aromatic solvent, preferably toluene, a chlorinated solvent, preferably dichloromethane, an ester, preferably ethyl acetate, an ether, preferably diethyl ether and tetrahydrofuran, a dipolar aprotic solvent, preferably dimethylformamide, an aliphatic solvent, preferably cyclohexane, an alcohol, preferably methanol or isopropanol, a ketone, preferably acetone, or a mixture thereof, either alone or with acetic acid, more preferably with dichloromethane, methanol or isopropanol or a mixture of acetone and glacial acetic acid; and thus enriched in the S,S isomer (the S,S:S,R ratio being higher than 95:5).

Step d) is carried out reacting compound (15) with carbonyldiimidazole in molar amounts ranging from 0.5 to 2, preferably from 0.9 to 1.2, in one of the same solvents as indicated for step a) except alcohols, at temperatures ranging After completion of the conversion of compound (15) into the two reactive species, ethanol is added to the reaction mixture which is left under stirring until complete disappearance of intermediates (18) and (19) (HPLC and NMR analysis). After evaporation of the solvents at reduced pressure, the residue is taken up with the same reaction solvent, then washed with water and the organic phase is evaporated to dryness. The resulting crude is subjected to the subsequent step.

Step e) is carried out with known methods. Preferably, the crude from step d) is dissolved in ethyl acetate and hydrochloric acid gas is bubbled therein at temperatures ranging from −10 to 10° C. After completion of the precipitation of benazepril hydrochloride, the residual hydrochloric acid is removed with conventional methods, after that the product is crystallized from acetone. Benazepril hydrochloride is obtained with diastereomeric purity above 99%.

The process of the present invention can also be conveniently carried out directly reacting intermediate of formula (16) in which R is ethyl (16a), obtained as described in b1 or in b2, with carbonyldiimidazole, in one of the solvents selected from those as indicated at step d), to give ethyl 3-(1-t-butoxycarbonylmethyl-2-oxo-2,3,4,5-tetrahydro-1H-benzo[b]azepin-3-yl)-2-oxo-6-phenyl-[1,3]oxazinan-4-carboxylate (20), as a mixture of the four possible diastereomers (SSS, SSR, SRS, SRR). Compound (20) is a novel compound and it forms part of the present invention. According to this variation, illustrated in Scheme 9, step e) comprises reaction with carbonyldiimidazole, then hydrogenation of compound (20) under the same conditions as indicated for step b) to give compound (12) as a S,S and S,R diastereomeric mixture. According to a preferred embodiment of the invention, step d) is carried out without isolating compound (16a), but filtering off the catalyst from the reaction mixture and adding carbonyldiimidazole. Analogously, compound (20) is not isolated from the mixture and, after addition of the catalyst, is directly subjected to catalytic hydrogenation.

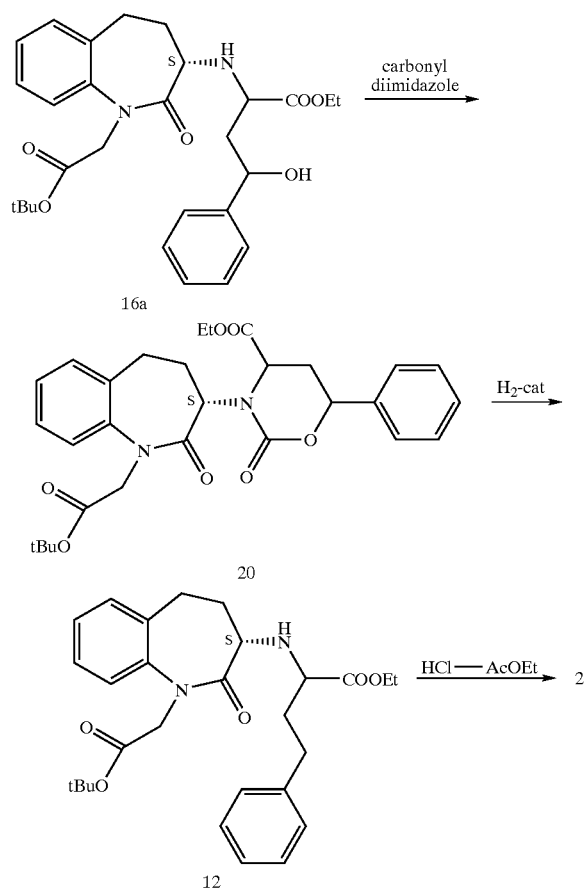

Scheme 9

Afterwards, step f) is carried out as described above.

The invention is illustrated in further detail by the following examples.

EXAMPLES

Example 1

Preparation of 3-[[1-(carboxy)-3-phenyl-propyl]amino]-1-t-butoxy-carbonylmethyl-2,3,4,5-tetrahydro-1H-benzazepin-2-one (15)

Ethyl 3-benzoylacrylate (13a) (55.6 g, 272 mmoles) is dropped into a solution of (3S)-3-amino-1-t-butoxycarbonylmethyl-2,3,4,5-tetrahydro-1H-benzazepin-2-one (11) (66.2 g, 228 mmoles) in 200 ml of ethyl acetate, at room temperature in 1 h. The resulting mixture is left under stirring for 18 h, added with 10% Pd—C (26 g, 22 mmoles) and hydrogenated at 3 atm for 18 h at room temperature. After completion of the reaction, 200 ml of acetic acid are added and the mixture is hydrogenated for a further 18 h at 3 atm and at room temperature. After this time, the catalyst is filtered off through Celite and the solvent mixture is evaporated to dryness, the residue is taken up in dichloromethane (200 ml) and the resulting precipitate is filtered, washed with 20 ml of dichloromethane and dried to give 3-[[1-(carboxy)-3-phenyl-propyl] amino]-1-t-butoxycarbonylmethyl-2,3,4,5-tetrahydro-1H-benzazepin- 2-one (15) (36 g, yield: 32%).

$^1$H-NMR (CDCl$_3$, δ in ppm): 1.42 (s, 9H), 2.03 (m, 3H), 2.38 (m, 1H), 2.57 (dd, 1H), 2.75 (m, 2H), 3.07 (t, 1H), 3.23 (m, 2H), 4.32 (d, 1H), 4.57 (d, H),7.05–7.40 (aromatics, 9H).

Example 2

Preparation of 3-[[1-(carboxy)-3-phenyl-propyl]amino]-1-t-butoxycarbonylmethyl-2,3,4,5-tetrahydro-1H-benzazepin-2-one (15)

Ethyl 3-benzoylacrylate (13a) (55.6 g, 272 mmoles) is dropped into a solution of (3S)-3-amino-1-t-butoxycarbonylmethyl-2,3,4,5-tetrahydro-1H-benzazepin-2-one (11) (66.2 g, 228 mmoles) in 200 ml of toluene, at room temperature in 1 h. The resulting mixture is left under stirring for 18 h, added with 10% Pd—C (26 g, 22 mmoles) and hydrogenated at 3 atm for 18 h at room temperature. After completion of the reaction, 200 ml of acetic acid are added and the mixture is hydrogenated for a further 18 h, at 3 atm at room temperature, after that the catalyst is filtered off through Celite and the solvent mixture is evaporated to dryness. The residue is taken up with isopropanol (500 ml) and the resulting precipitate is filtered, washed with 20 ml of dichloromethane and dried to give 3-[[1-(carboxy)-3-phenyl-propyl]amino]-1-t-butoxycarbonylmethyl-2,3,4,5-tetrahydro-1H-benzazepin-2-one (15) (58.5 g, yield: 52%).

Example 3

Preparation of 3-[[1-(carboxy)-3-phenyl-propyl]amino]-1-t-butoxycarbonylmethyl-2,3,4,5-tetrahydro-1H-benzazepin-2-one (15)

Ethyl 3-benzoylacrylate (13a) (55.6 g, 272 mmoles) is dropped into a solution of (3S)-3-amino-1-t-butoxycarbonylmethyl-2,3,4,5-tetrahydro-1H-benzazepin-2-one (11) (66.2 g, 228 mmoles) in 200 ml of toluene, at room temperature in 1 h. The resulting mixture is left under stirring for 18 h, then added with 10% Pd—C (26 g, 22 mmoles) and hydrogenated at 3 atm for 18 h at room temperature. After completion of the reaction the catalyst is filtered off through Celite, 50 ml of acetic acid are added and the solvent mixture is evaporated to kettle temperature of 110–120° C. The residue is taken up in 200 ml of toluene, 50 ml of acetic acid then cyclohexene (50 ml) and 10% Pd—C (26 g, 22 mmoles) are added. The reaction mixture is heated to 80° C. for 18 h, after that the catalyst is filtered off through Celite and solvents are evaporated off. The residue is taken up with isopropanol (500 ml) and the resulting precipitate is filtered, washed with 20 ml of isopropanol and dried to give 3-[[1-(carboxy)-3-phenyl-propyl] amino]-1-t-butoxycarbonylmethyl-2,3,4,5-tetrahydro-1H-benzazepin-2-one (15) (60.7 g, yield: 54%).

Example 4

Preparation of 3-[[1-(carboxy)-3-phenyl-propyl] amino]-1-t-butoxycarbonylmethyl-2,3,4,5-tetrahydro-1H-benzazepin-2-one (15)

Ethyl 3-benzoylacrylate (13a) (55.6 g, 272 mmoles) is drooped into a solution of (3S)-3-amino-1-t-butoxycarbonylmethyl-2,3,4,5-tetrahydro-1H-benzazepin-2-one (11) (66.2 g, 228 mmoles) in 200 ml of toluene, at room temperature in 1 h. The resulting mixture is left under stirring for 18 h, then a solution of sodium borohydride (228 mmoles 8.6 g) and tetrabutylammonium chloride (5.0 g) in 50 ml of 0.1 M NaOH is added and the mixture is stirred at room temperature for 18 h. The aqueous phase is separated, 50 ml of acetic acid are added to the organic phase and the mixture is left under stirring for 30', then added with 10% Pd—C (26 g, 22 mmoles) and ammonium formate (456 mmoles, 33.3 g) and left under stirring for 4 h. Afterwards, the catalyst is filtered off through Celite and 100 ml of water is added. The resulting precipitate is filtered, washed with 20 ml of isopropanol and dried to give 3-[[1-(carboxy)-3-phenyl-propyl]amino]-1-t-butoxycarbonylmethyl-2,3,4,5-tetrahydro-1H-benzazepin-2-one (15) (53.9 g, yield: 48%).

Example 5

Preparation of benazepril hydrochloride (2)

25 g (55.2 mmoles) of 3-[[1-(carboxy)-3-phenyl-propyl] amino]-1-t-butoxycarbonyl-methyl-2,3,4,5-tetrahydro-1H-benzazepin-2-one (15) are suspended in 250 ml of toluene and added with carbonyldiimidazole (10.74 g, 66.2 mols). The mixture is left under stirring for 2 h, then 100 ml of ethanol are added. After reacting for 4 h, solvents are evaporated off and the residue is taken up with 300 ml of toluene and 100 ml of water. The phases are separated and the organic phase is washed twice with water. Toluene is then evaporated off and the mixture is taken up with 75 ml of ethyl acetate, cooled to 11° C. and HCl gas is bubbled therein. After precipitation of the product, about ⅔ of the solvent are distilled off twice, adding each time fresh solvent to remove the residual HCl, then the mixture is diluted with 75 ml of acetone, cooled to 10° C. and filtered, to obtain 21.4 g of product (84% yield).
$^1$H NMR (D$_2$O, 6 in ppm): 1.02 (t, 3H), 2.17 (m, 3H), 2.43 (m, 1H), 2.61 (m, 3H), 2.97 (m, 1H), 3.77 (m, 2H), 3.97 (q, 2H), 4.36 (d, 1H), 4.57 (d, 1H),7.05–7.35 (aromatics, 9H).

Example 6

Preparation of benazepril hydrochloride (2)

Ethyl 3-benzoylacrylate (13a) (55.6 g, 272 mmoles) is dropped into a solution of (3S)-3-amino-1-t-butoxycarbonylmethyl-2,3,4,5-tetrahydro-1H-benzazepin-2-one (11) (66.2 g, 227 mmoles) in 200 ml of toluene, at room temperature in 1 h. The resulting mixture is left under stirring for 18 h, then added with 10% Pd—C (26 g, 22 mmoles) and hydrogenated at 3 atm for 18 h at room temperature. The catalyst is filtered off and carbonyldiimidazole (272 mmoles, 44.2 g) is added. After reacting for 4 h the mixture is washed 3 times with 100 ml of water, added again with 10% Pd—C (26 g, 22 mmoles) and hydrogenated at 1 atm for 18 h at room temperature. After that the catalyst is filtered off, the solvent is evaporated off and the residue is taken up with 240 ml of ethyl acetate, cooled to 10° C. and HCl gas is bubbled therein to complete precipitation of the product. About ⅔ of the solvent is distilled off twice, adding each time fresh solvent to remove the residual HCl. The mixture is then diluted with 75 ml of acetone, cooled to 10° C. and filtered, to obtain 32 g of product (31% yield).
$^1$H NMR (D$_2$O, δ in ppm): 1.02 (t, 3H), 2.17 (m, 3H), 2.43 (m, 1H), 2.61 (m, 3H), 2.97 (m, 1H), 3.77 (m, 2H), 3.97 (q, 2H), 4.36 (d, 1H), 4.57 (d, 1H),7.05–7.35 (aromatics, 9H).

Example 7

Preparation of 3-[[1-(ethoxycarbonyl)-3-oxo-3-phenyl-propyl] -amino]-1-t-butyl-oxycarbonylmethyl-2, 3,4,5-tetrahydro-1H-benzazepin-2-one (14)

Ethyl 3-benzoylacrylate (13a) (55.6 g, 272 mmoles) is dropped into a solution of (3S)-3-amino-1-t-butoxycarbonylmethyl-2,3,4,5-tetrahydro-1H-benzazepin-2-one (11) (66.2 g, 227 mmoles) in 200 ml of toluene, at room temperature in 1 h. The resulting mixture is left under stirring for 18 h, then solvent is evaporated off and the residue is purified by chromatography (eluent hexane-ethyl acetate 7:3). Two isomeric products are isolated.
Isomer 1 (first eluted)—minor product (SR):
$^1$H-NMR (CDCl$_3$, 6 in ppm): 1.17 (t, 3H), 1.40 (s, 9H), 1.92 (m, 1H), 2.30 (m, 1H), 2.55 (dd, 1H), 3.32 (m,4H), 3.72 (t, 1H), 4.08 (q, 2H), 4.23 (d, 1H), 4.66 (d, 1H),7.05–8.00 (aromatics, 9H).
Isomer 2 (second eluted)—main product (SS):
$^1$H-NMR (CDCl$_3$, δ in ppm): 1.05 (t, 3H), 1.40 (s, 9H), 1.98 (m, 1H), 2.38 (m, 1H), 2.57 (dd, 1H), 3.35 (m, 4H), 3.64 (t, 1H), 4.02 (q, 2H), 4.24 (d, 1H), 4.53 (d, 1H),7.05–8.00 (aromatics, 9H).

Example 8

Preparation of 3-[[1-(ethoxycarbonyl)-3-hydroxy-3-phenyl-propyl] amino]-1-t-butoxycarbonylmethyl-2, 3,4,5-tetrahydro-1H-benzazepin-2-one (16)

Ethyl 3-benzoylacrylate (13a) (55.6 g, 250 mmoles) is dropped into a solution of (3S)-3-amino-1-t-butoxycarbonylmethyl-2,3,4,5-tetrahydro-1H-benzazepin-2-one (11) (66.2 g, 227 mmoles) in 200 ml of toluene, at room temperature in 1 h. The resulting mixture is left under stirring for 18 h, then added with 10% Pd—C (26 g, 22 mmoles) and hydrogenated at 3 atm for 18 h at room temperature. The solvent is evaporated off and the residue is purified by chromatography (eluent: hexane-ethyl acetate 7:3). A mixture of isomeric products is isolated.

$^1$H-NMR (CDCl$_3$, δ in ppm): 1.03–1.32 (m, 3H), 1.40 (m, 9H), 1.73–1.93 (m, 1H), 1.95–2.15 (m, 1H), 2.38–2.63 (m, 2H), 3.18–3.43 (m,4H), 3.98–4.12 (m, 2H), 4.25–4.60 (m, 2H), 4.68–5.20 (m, 1H), 7.05–7.40 (aromatics, 9H).

Example 9

Preparation of ethyl 3-(1-t-butoxycarbonylmethyl-2-oxo-2,3,4,5-tetrahydro-1H-benzo[b]azepin-3-yl)2-oxo-6-phenyl-[1,3]oxazinan-4-carboxylate (20)

Ethyl 3-benzoylacrylate (13a) (55.6 g, 250 mmoles) is dropped into a solution of (3S)-3-amino-1-t-butoxycarbonylmethyl-2,3,4,5-tetrahydro-1H-benzazepin-2-one (11) (66.2 g, 227 mmoles) in 200 ml of toluene, at room temperature in 1 h. The resulting mixture is left under stirring for 18 h, then added with 10% Pd—C (26 g, 22 mmoles) and hydrogenated at 3 atm for 18 h at room temperature. The catalyst is filtered off and carbonyldiimidazole (272.4 mmoles, 44.16 g) is added. After reacting for 4 h the mixture is washed 3 times with 100 ml of water. After completion of the reaction the solvent is evaporated off and the residue is purified by chromatography (eluent: hexane-ethyl acetate 7:3). A mixture of isomeric products is isolated.

$^1$H-NMR (CDCl$_3$, δ in ppm): 1.03–1.32 (m, 3H), 1.40 (m, 9H), 1.83–2.40 (m, 5H), 3.05–3.37 (m, 3H), 3.95–4.08 (m, 2H), 4.17–4.62 (m, 2H), 5.90–6.20 (m, 1H), 7.05–7.40 (aromatics, 9H).

Example 10

Preparation of [2-oxo-3-(2-oxo-5-phenyl-tetrahydro-furan-3-ylamino)-2,3,4,5-tetrahydro-benzo[b]azepin-1-yl]-acetic acid tert-butyl ester (17)

Ethyl 3-benzoylacrylate (13a) (55.6 g, 250 mmoles) is dropped into a solution of (3S)-3-amino-1-t-butoxycarbonylmethyl-2,3,4,5-tetrahydro-1H-benzazepin-2-one (11) (66.2 g, 227 mmoles) in 200 ml of toluene, at room temperature in 1 h. The resulting mixture is left under stirring for 18 h, then added with 10% Pd—C (26 g, 22 mmoles) and hydrogenated at 3 atm for 18 h at room temperature. After completion of the reaction, the catalyst is filtered off, 50 ml of acetic acid are added and volatiles are distilled off at 110–120° C. inner temperature.

The residue is purified by chromatography (eluent: hexane-ethyl acetate 7:3) to obtain a mixture of isomeric products.

$^1$H-NMR (CDCl$_3$, δ in ppm): 1.45 (m, 9H), 1.82–2.15 (m, 2H), 2.41–2.63 (m, 3H), 3.18–3.43 (m, 1H), 3.18–3.95 (m, 2H), 4.25–4.60 (m, 2H), 5.15–5.70 (m, 1H),7.05–7.40 (aromatics, 9H).

Example 11

Preparation of 3-[[1-(carboxy)-3-phenyl-propyl]amino]-1-t-butoxycarbonylmethyl-2,3,4,5-tetrahydro-1H-benzazepin-2-one (15)

Ethyl 3-benzoylacrylate (13a) (55.6 g, 272 mmoles) is dropped into a solution of (3S)-3-amino-1-t-butoxycarbonylmethyl-2,3,4,5-tetrahydro-1H-benzazepin-2-one (11) (66.2 g, 228 mmoles) in 200 ml of toluene, at room temperature in 1 h. The resulting mixture is left under stirring for 18 h, then added with 10% Pd—C (26 g, 22 mmoles) and hydrogenated at 3 atm for 18 h at room temperature. After completion of the reaction the catalyst is filtered off through Celite, 100 ml of acetic acid are added and the solvent mixture is reacted at 20–30° C. for 18 h. After lactonization to compound (17), ammonium formate (51.4 g, 816 mmoles) and 10% Pd—C (26 g, 22 mmoles) are added. The reaction mixture is heated to 40° C. for 3 h, after that the catalyst is filtered off through Celite and solvents are evaporated off. The residue is taken up with acetone (600 ml) and acetic acid (200 ml), heated to dissolution and cooled. The resulting precipitate is filtered, washed with 80 ml of acetone1 and dried to give 3-[[1-(carboxy)-3-phenyl-propyl]amino]-1-t-butoxycarbonylmethyl-2,3,4,5-tetrahydro-1H-benzazepin-2-one (15) (60.7 g, yield: 54%).

What is claimed is:

1. A process for the preparation of benazepril hydrochloride (2),

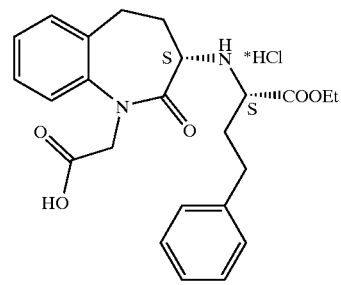

2 comprising the following steps:
a) reacting (3S)-3-amino-1-t-butoxycarbonylmethyl-2,3,4,5-tetrahydro-1H-benzazepin-2-one (11)

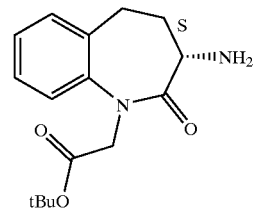

11 with a 3-benzoyl acrylic acid ester (13)

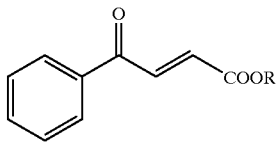

13 in which R is a straight or branched C$_1$–C$_6$ alkyl group or a benzyl group,
to give a Michael adduct of formula (14)

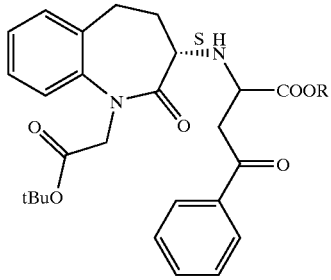

in which R has the meanings as defined above;

b) transforming compound (14) into 3-[[1-(ethoxycarbonyl)-3-hydroxy-3-phenyl-propyl]amino]-1-t-butoxycarbonylmethyl-2,3,4,5-tetrahydro-1H-benzazepin-2-one (15)

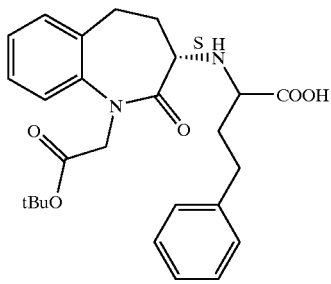

c) crystallizing the S,S isomer of compound (15);

d) esterifying compound (15) to give 3-[[1-(ethoxycarbonyl)-3-phenyl-propyl]amino]-1-t-butoxycarbonylmethyl-2,3,4,5-tetrahydro-1H-benzazepin-2-one (12); and

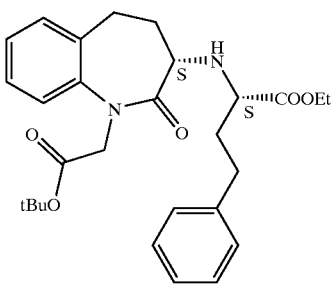

e) treating compound (12) with hydrochloric acid gas to give benazepril hydrochloride (2).

2. A process as claimed in claim 1 wherein R is ethyl.

3. A process as claimed in claim 1 wherein step b) is carried out without isolating compound (14).

4. A process according to claim 1 wherein step b) comprises:

catalytic hydrogenation of compound (14) to give an intermediate of formula (16)

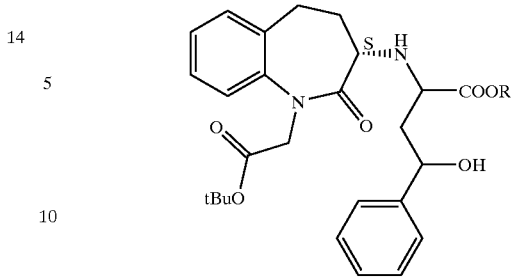

in which R has the meanings as defined above; and catalytic hydrogenation of compound (16) in the presence of a mineral or organic acid to give compound (15).

5. A process as claimed in claim 4 wherein the mineral acid is sulfuric acid and the organic acid is acetic acid.

6. A process as claimed in claim 1 wherein step b) comprises:

catalytic hydrogenation of compound (14) to give compound (16);

conversion of compound (16) to lactone (17); and

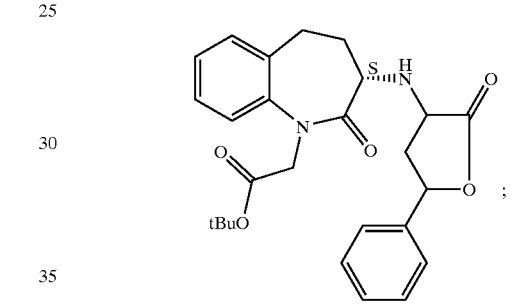

conversion of compound (17) to compound (15) by catalytic hydrogenation or by hydrogen transfer reaction.

7. A process as claimed in claim 6 wherein compound (16) is converted to lactone (17) by addition of acetic acid and heating to a temperature ranging from 0° C. to 120° C.

8. A process as claimed in claim 6 wherein compound (14) is directly converted to lactone (17) by reduction with sodium borohydride.

9. A process as claimed in claim 4 wherein the catalyst is Pd supported on charcoal.

10. A process as claimed in claim 6 wherein the hydrogen transfer reaction comprises the use of a hydrogen donor selected from cyclic ethers, cyclohexene, cyclohexadiene, methylcyclohexene, limonene, dipentene, mentene, hydrazine, phosphinic acid and derivatives, indoline, ascorbic acid, formic acid and the sodium or ammonium salts thereof, secondary alcohols.

11. A process as claimed in claim 10 wherein the hydrogen donor is ammonium formate.

12. A process as claimed in claim 1, wherein step c) crystallization is carried out in a mixture of acetone and acetic acid, as solvent.

13. A process as claimed in claim 1 wherein steps a) and b) are carried out in a solvent selected from toluene, dichloromethane, ethyl acetate, diethyl ether, tetrahydrofuran, dimethylformamide, cyclohexane, methanol and acetone, and step d) is carried out in a solvent selected from toluene, dichloromethane, ethyl acetate, diethyl ether, tetrahydrofuran, dimethylformamide, cyclohexane and acetone.

14. A process as claimed in claim 13, wherein the solvent is toluene.

15. A process as claimed in claim 1 wherein step d) is carried out reacting compound (15) with carbonyldiimidazole and ethanol.

16. A process as claimed in claim 4 wherein compound (16) in which R is ethyl is treated with carbonyldiimidazole to give ethyl 3-(1-t-butoxycarbonylmethyl-2-oxo-2,3,4,5-tetrahydro-1H benzo[b]azepin-3-yl)-2-oxo-6-phenyl-[1,3]oxazinan-4-carboxylate (20)

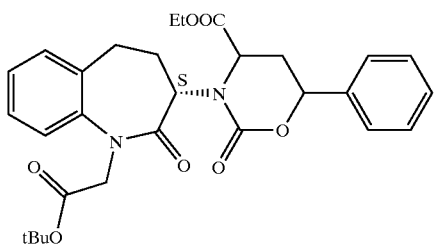

20 which is subjected to catalytic reduction to give compound (12).

17. A process according to any one of claim 1 wherein the catalytic reductions or hydrogen transfer reactions are carried out in the presence of a catalyst selected from Pd, Pt, Rh, Ru, Cu on a support selected from charcoal, alumine, barium sulfate, calcium carbonate.

18. A process as claimed in claim 16 wherein the catalytic reduction is carried out without isolating compound (20).

19. A compound selected from the group consisting of:

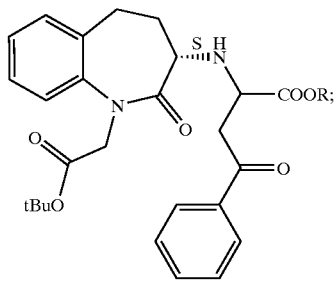

14

-continued

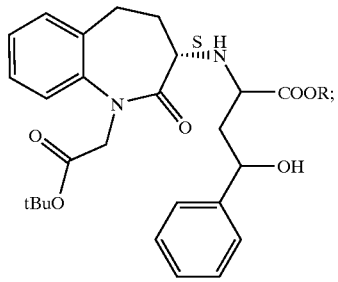

16

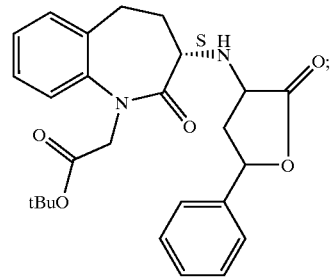

17

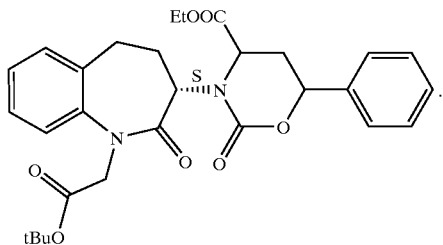

20 in which R is a straight or branched $C_1$–$C_6$ alkyl group or a benzyl group.

* * * * *